United States Patent [19]

Au et al.

[11] Patent Number: 4,830,827
[45] Date of Patent: May 16, 1989

[54] METHOD OF INHIBITING CORROSION USING PERHYDRO-S-TRIAZINE DERIVATIVES

[75] Inventors: Andrew T. Au, Needham, Mass.; Hugh F. Hussey, Novi, Mich.

[73] Assignee: The Dow Chemical Company, Midland, Mich.

[21] Appl. No.: 848,359

[22] Filed: Jun. 4, 1986

Related U.S. Application Data

[63] Continuation-in-part of Ser. No. 602,779, Apr. 23, 1984, Pat. No. 4,605,737.

[51] Int. Cl.$^4$ .................. C23F 11/12; C23F 11/04
[52] U.S. Cl. ............................................. 422/7; 422/12; 422/16; 252/8.555; 252/384; 252/394
[58] Field of Search ............................. 422/7, 12, 16; 252/8.555, 542, 384, 394

[56] References Cited

U.S. PATENT DOCUMENTS

| | | |
|---|---|---|
| 2,889,277 | 6/1959 | Hughes . |
| 3,819,527 | 6/1974 | Hayman, Jr. . |
| 4,266,054 | 5/1981 | Au . |
| 4,308,031 | 12/1981 | Au . |
| 4,402,907 | 8/1983 | Clark ........................................ 422/7 |
| 4,605,737 | 8/1986 | Au ........................................ 544/215 |

OTHER PUBLICATIONS

*Chemical Abstracts*, 87:105567q, p. 201, vol. 87, 1977.
J. A. Bell et al., *J. Chem., Soc.* c 11, 1556–8 (1969).

*Primary Examiner*—Barry S. Richman
*Assistant Examiner*—Timothy M. McMahon

[57] ABSTRACT

Included are novel perhydro-s-triazine derivatives, tentacular-perhydro-s-triazines. For example, 1,3,5-triazine-1,3,5-(2H,4H,6H)triethanol dioleate; 1,3,5-triazine-1,3,5-(2H,4H,6H)triethanethiol trioleate; and 1,3,5-triazine-1,3,5-(2H,4H,6H)tris(morpholinoethane) are included. The derivatives are corrosion inhibitors for metals. The compounds may also be used as emulsifiers, lubricants and hydraulic fluids.

12 Claims, No Drawings ns # METHOD OF INHIBITING CORROSION USING PERHYDRO-S-TRIAZINE DERIVATIVES

CROSS-REFERENCE TO RELATED APPLICATION

This application is a continuation-in-part of copending U.S. patent application Ser. No. 602,779, filed Apr. 23, 1984 now U.S. Pat. No. 4,605,737.

FIELD

This invention concerns compositions of matter which are derivatives of heterocyclic polyazines and a process to prepare the derivatives. The invention also concerns use of said compositions, for example, as a corrosion inhibitor.

BACKGROUND

It is generally recognized that oil-producing formations often yield brine with the crude oil. This brine may be extremely corrosive in its action upon the oil-producing and collecting equipment, including the metal tubing, casings, pumps, pipe lines, and storage equipment. This type of corrosion is particulatly noticeable in wells producing brine which contain varying amounts of hydrogen sulfide, carbon dioxide and other acidic materials therein.

Considerable effort has been directed in the past to reducing the cost of maintaining production and collection equipment free of corrosion by introducing into the well various corrosion inhibitors including formaldehyde, nitrogen bases of various types, amines, and combinations of the foregoing compounds.

Hughes, U.S. Pat. No. 2,889,277 (1959) and Hayman, Jr., U.S. Pat. No. 3,819,527 (1974) disclose certain tri(N-aryl)perhydro-s-triazine compounds for use as corrosion inhibitors in aqueous systems such as crude oil streams or acid pickling baths.

In *Chemical Abstracts* 87:105567q, 1,3,5-tris(2-hydroxyethyl)triazine is disclosed to be a suitable additive to sheet metal rolling lubricants to inhibit microbial growth which induces metal corrosion.

Certain ester derivatives of perhydro-s-triazine are known. In J. A. Bell et al., *J. Chem. Soc.* c 11, 1556-8 (1969), there is disclosed the compound 1,3,5-triazine-1-(2H)-methanol, tetrahydro-3,5-dinitro-, acetate corresponding to the formula:

$$O_2N-N\overbrace{\phantom{xxx}}^{\phantom{x}}N-CH_2OC(O)CH_3$$
$$\underbrace{\phantom{xxxxxx}}_{\displaystyle\mathop{N}_{\displaystyle|}}$$
$$NO_2$$

Also known are 1,3,5-tris(2-hydroxyethyl)perhydro-s-triazines disclosed by Au in U.S. Pat. Nos. 4,266,054 (1981) and 4,308,031 (1981) (each incorporated herein by reference). The compounds were found to be useful solubilizing agents such as in solubilizing alkali or alkaline earth metal salts in organic media.

SUMMARY

In one aspect, the present invention provides novel perhydro-s-triazine derivatives, tentacular-perhydro-s-triazines. Said derivatives may be prepared by a process comprising contacting a suitable compound or mixture of compounds which contains a primary amino group with formaldehyde, thereupon which, if desired or necessary, contacting with a tentacular-perhydro-s-triazine derivatizing agent, under conditions sufficient to prepare said derivatives, which is another aspect of the invention. Still another aspect of the invention is the method of use of the tentacular-perhydro-s-triazines.

The derivatives can be used for effective corrosion inhibitors for metals. They are highly effective with iron-containing metals such as steel in contact with acid-containing solutions such cleaning solutions used to clean or rid metallic surfaces of oxide scale or other undesired deposits such as oil or brine solutions. The derivatives are also useful in solubilizing of alkali and alkaline earth metal salts in organic media such as liquids. The derivatives can additionally be employed as emulsifiers, lubricants and hydraulic fluids or as additives thereto.

ILLUSTRATIVE EMBODIMENTS

The tentacular-perhydro-s-triazines include those corresponding to the general formula:

$$(R)_r[Q(CHR^1)_m]_q N\overbrace{\phantom{xxx}}^{\phantom{x}} N[(CHR^1)_mQ]_q(R)_r$$
$$\underbrace{\phantom{xxxxxx}}_{\displaystyle\mathop{N}_{\displaystyle|}}$$
$$(CHR^1)_m$$
$$|$$
$$Q$$

wherein

R is separately at each occurrence hydrogen or an organic moiety, preferably of about 100 carbons or less;

r is separately at each occurence zero or one;

Q is preferably separated at each occurrence a $C_{1-60}$ (i.e., from one to about sixty carbons) moiety such as acyclic secondary and tertiary amino, heterocyclic secondary and tertiray amino, hydroxy-substituted and mercapto-substituted acyclic and heterocyclic secondary and tertiary amino, amido (i.e., —NC(O)—), acyl (i.e., —OC(O)—), thioacyl (i.e., —SC(O)—), ether, thioether, mercapto (i.e., —SH) and other generally inertly—substituted variants thereof;

q is separately at each occurrence zero or one, preferably one, with the provision that when q is one, the value of r of the adjacent R moiety is zero, and if q is zero, R is an organic moiety;

$R^1$ is separately at each occurrence a moiety such as hydrogen or $C_{1-20}$ organic, preferably hydrogen or $C_{1-20}$ alkyl, most preferably hydrogen; and m is separately at each occurrence an integer from one to about twenty, more preferably from two to four, and most preferably two.

Preferred Q moieties include tertiary amino moieties such as tertiary alkyl amino moieties; heterocyclic amino moieties such as found in piperazino moieties; hydroxy amino moieties such as tertiary alkylhydroxyl amino moieties; amido moieties such as fatty acid amido moieties; ester and thioester moieties such as fatty acid ester and thioester moieties; ether and thioether moieties such as aliphatic ether and thioether moieties; carboxylic acid moieties such as aliphatic carboxylic acid moieties; and combinations thereof, for example, moieties such as ester-carboxylic acid moieties and morpholino moieties. Most preferred Q moieties are the nitrogen- and oxygen-containing Q moieties of the general formula —$NR^2_2$; —$NR^2(C(O)R^2)$; —$N(C(O)R^2_2$; —$NR^3$; and —OH; —$OR^2$ and —$O(C(O)R^2$ wherein $R^2$ is hydrocarbyl or oxygen-substituted hydrocarbyl generally of up to about 30 carbons; and $R^3$ is a bivalent hydrocarbyl or nitrogen- or oxygen-substituted hydrocarbyl generally of up to about 30 carbons which forms a heterocyclic ring containing said nitrogen (of $NR^3$).

Examples of $R^2$ include methyl, ethyl, heptadecyl, benzyl, 4-methylbenzyl, 2-hydroxyethyl, acetonyl, and 2-(carboxylic acid)ethyl. Examples of $R^3$ include penta(methylene), bis(ethylene)ethylamino, and bis(ethyleneyl)epoxy, which thus represent respectively the $NR^3$ moieties piperidinyl, 1-(4-ethyl)piperazinyl and morpholino.

By generally inertly-substituted is meant a chemical substitution product which, in general, does not interfere with the preparation of the tentacular-perhydro-s-triazine. For example, any of the types of Q moieties can be substituted onto another, provided that (as is always the case) any recited carbon limits for the overall Q moiety (for example, upper limit of about 60 carbons) are maintained.

Preferred tentacular-perhydro-s-triazines include tris(hydroxyalkyl)-perhydro-s-triazine long-chain ester and ester-ether derivatives of the following formula:

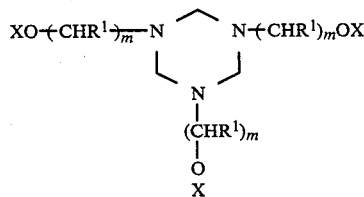

and X includes hydrogen, $+(CHR^1)_2-O+_nR^4$ and —$C(O)R^2$ where n is an integer from zero to about four, and $R^4$ is alkyl, cycloalkyl, alkenyl, aryl, alkylaryl, alkenylaryl, arylalkyl or arylalkenyl of up to about 30 carbons, provided that in at least one occurrence, X is —$C(O)R^4$. Preferably therein, $(CHR^1)_m$ is —$(CH_2)(CHR^1)_{(m-1)}$. More preferably therein, especially such as disclosed in said copending parent U.S. patent application Ser. No. 602,779, now U.S. Pat. No. 4,605,737, (incorporated herein by reference), $R^1$ is independently at each occurrence methyl, ethyl or H, and m is two, and most preferably therein $R^1$ is hydrogen.

Preferred tentacular-perhydro-s-triazines also include tris(piperazino)-perhydro-s-triazines of the following formula:

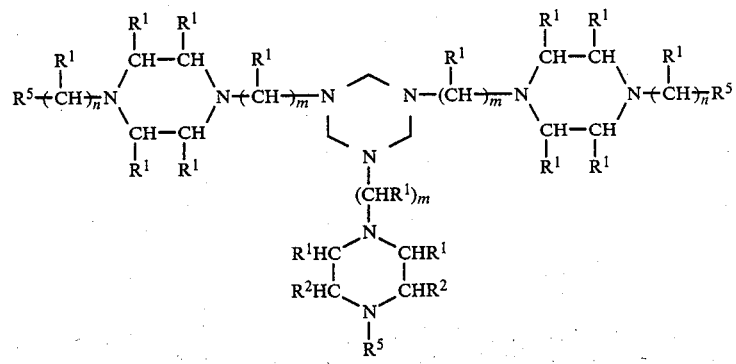

wherein $R^5$ is separately at each occurrence hydrogen, $C_{1-30}$ hydrocarbyl, $(CHR^1)_nR^4$, —$C(O)R^2$ or, if n is positive, —$NR^2$, and n is an integer from zero to about four. Preferably, $R^1$ is hydrogen. Preferably $R^5$ is separately at each occurrence $C_{1-20}$ hydrocarbyl (hence, ($C_{1-20}$ hydrocarbyl)piperazino), a carboxyl moiety of the general formula —$C(O)R^2$ wherein $R^2$ is a $C_{1-20}$ hydrocarbyl moiety. Most preferably, $R^5$ is methyl or ethyl, and n is zero.

Preferred tentacular-perhydro-s-triazines also include tris(amido)-perhydro-s-triazines of the following formula:

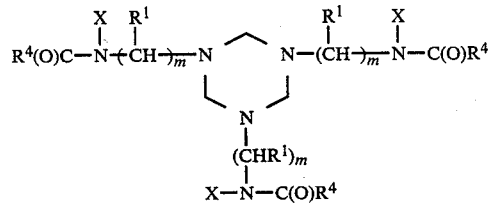

wherein X is hydrogen or $R^2$. Preferably, $R^2$ is $C_{1-20}$ hydrocarbyl and most preferably methyl or ethyl.

Preferred tentacular-perhydro-s-triazines also include combinations such as, for example, bis(ester)(amido)-perhydro-s-triazines; bis(amido)morpholino)-perhydro-s-triazines; bis(morpholino)(hydroxyamino)-perhydro-s-triazines; bis(ether)(amido)-perhydro-s-triazines; (ester)(morpholino)(amido)-perhydro-s-triazines; (ester)-(amido)(hydroxy)-perhydro-s-triazines.

The tentacular-perhydro-s-triazines can be prepared by a process comprising reacting formaldehyde with a suitable compound, or mixture of compounds, which contains a primary amino group. The reaction product, particularly when containing an additional active hydrogen moiety such as, for example, in a hydroxyl moiety, may be reacted with a suitable derivatizing agent. The conditions are those sufficient to prepare the tentacular-perhydro-s-triazines.

By suitable compound is meant a compound which, when reacted (solely or as one of a plurality of compounds which contain the compound with the primary amino group) with the formaldehyde, forms the tentacular-perhydro-s-triazines. For example, aniline by itself reacted with formaldehyde will form 1,3,5-triazine-(2H,4H,6H)-1,3,5-tribenzene which is not a tentacular-perhydro-s-triazines, and thus aniline by itself is not a suitable compound. However, a mixture of aniline and 2-aminoethyl piperazine may react to form 1,3,5-triazine-(2H,4H,6H)-1,3,-bis(benzene)-5-[2'(1-piperazineethane)]which is a tentacular-perhydro-s-triazine. Thus, this mixture contains a suitable compound which contains a primary amino group, and this mixture is suitable for preparing the tentacular-perhydro-s-triazines.

Examples of preferred suitable compounds include primary amines such as, for example, methylamine; 1-aminodecane; (aminomethyl)cyclohexane; benzylamine; 1-(4-methylphenyl)-2-aminoethane and 1-phenyl-2-aminopropane. Also included are other organic compounds which contain a primary amino group such as alkanolamines, for example, 2-aminoethanol; 2-amino-1-propanol; 3-amino-1-butanol; other hydroxylamines such as for example, 2-amino-1-phenyl-1-butanol and 1-4(4-hydroxyphenyl)-2-propylamine; other oxygen-containing compounds with a primary amino group such as amino ethers; amino thiols such as, for example, 2-aminoethylmercaptan; and other sulfur-containing compounds with a primary amino group.

After the contact of the suitable compound containing the primary amino group to form the reaction product, the reaction product may be further reacted, for example, if it contains an additional active hydrogen moiety. The further reaction is with the tentacular-perhydro-s-triazine derivatizing agent, which is a chemical means for preparing a derivative of the reaction product, the derivative being a tentacular-perhydro-s-triazine.

Examples of preferred tentacular-perhydro-s-triazine derivatizing agents can include so-called alkylating agents which react with the active hydrogen of a moiety such as the N, O or S moieties (as customary, said alkylating agents not restricted to agents which merely introduce saturated hydrocarbyl moieties). In the case of N moieties, preferred alkylating agents include agents such as methyl chloride; α-bromotoluene; n-butyl chloride. In the case of O moieties, preferred alkylating agents include Grignard reagents. In the case of S moieties, preferred alkylating agents include alkylating agents such as aldehydes and 1-alkenes.

The tentacular-perhydro-s-triazine derivatizing agent can be a halogenating agent. For example, it can be bromine, used to halogenate unsaturated carbon to carbon bonds, for example, double bonds (i.e., C=C).

Preferred derivatizing agents also include etherating agents such as epoxides such as 1,2-ethane oxide; 1,2-propylene oxide; 1,2-butylene oxide and allyl glycidyl ether, which are reacted with the active hydrogen-containing moieties to prepare compounds such as ethers, and other etherating agents such as by reaction of the O moieties with reagents of a standard Williamson ether synthesis.

Morpholino functionality can be incorporated by reaction of a morpholinoamine and formaldehyde. For example, 2-morpholinoethylamine can be employed to prepare the morpholino-substituted tentacular-perhydro-s-triazines.

Preferred derivatizing agents also include acylating agents such as transesterification agents and acylating agents such as carboxylic acid halides such as acetyl chloride; benzoyl chloride and octanoyol chloride; carboxylic acid ester halides such as ethyl chloroformate and benzyl chloroformate; carboxylic acid anhydrides such as acetic anhydride; propionic anhydride and succinic anhydride.

Ester (thioester) and amido derivatives are preferably prepared by acylation. Thus, hydroxy (mercapto) or the appropriate amino perhydro-s-triazine can be acylated (thioacylated) or amidated, and, for example, optionally etherated as desired, with a derivatizing agent selected from the group consisting of acylating agents and optionally agents such as, for example, etherating agents such as epoxides, under reaction conditions sufficient to carry out the process involving the acylations.

The ester interchange is preferably conducted under conditions of high vacuum (the rate may be increased by the use of a phase-transfer catalyst). A preferred process for preparing esters involves the reaction of a carboxylic acid chloride or the like acyl compound with a hydroxy perhydro-s-triazine (e.g., a tris-hydroxyalkyl perhydro-s-triazine) in the presence of potassium carbonate.

A more preferable method for preparing esters is transacylation such as, for example, the transesterification of corresponding fatty acid lower alkyl esters, such as methyl and ethyl esters, with the hydroxyalkyl perhydro-s-triazine. This transesterification is carried out in the presence of a base strong enough to generate an alkoxide ion such as an alkaline earth or an alkali metal hydroxide (e.g., NaOH, KOH) or oxide, or a metal alkoxide or metal hydrides (e.g., NaH). The corresponding lower alcohol is typically produced, which may be conveniently removed during and after this transesterification by methods such as distillation.

The molar ratio of the hydroxyalkyl perhydro-s-triazine to base is such that the ester derivative is produced. Preferable molar ratios of the hydroxyalkyl perhydro-s-triazine to base include ratios from abut 10:1 to about 1:10 and most preferably from about 1:1 to about 1:3.

Pressures of the lower alkyl ester transesterification are such that tentacular-perhydro-s-triazine ester derivatives are produced. Pressures are preferably reduced. Reduced pressures include pressures below about one atmosphere. Preferable reduced pressures are about 100 mm Hg (13.3 kPa) or below, more preferably about 20 mm Hg (2.66 kPa) or below and most preferably about 1 mm Hg (0.133 kPa) or below. An especially preferred reduced pressure is about 0.1 mm Hg (0.0133 kPa) or below. Thus, the lower alcohol may be conveniently removed.

Temperatures of the lower alkyl ester transesterification are such that tentacular-perhydro-s-triazine ester derivatives are produced. Temperatures are preferably elevated. Elevated temperatures includes temperatures about 30° C. or above. Preferable upper limits of preferred ranges of elevated temperatures are about 150° C., most preferably about 90° C. More preferable lower limits of preferred ranges of elevated temperatures are about 50° C. and most preferably about 70° C.

Time of the lower alkyl ester transesterification reaction is such that tentacular-perhydro-s-triazine ester derivatives are produced. Typical times may include times up to 24 hours. More preferably, the time of reaction is less than about 12 hours.

The lower alkyl ester transesterification reaction may be conducted neat or in the environment of a liquid diluent preferably such as a higher boiling polar but nonhydroxylated liquid such as, for example, pyridine, dimethyl sulfoxide, dimethyl formamide and glycol ethers such as, for example, diethylene glycol dimethyl ether.

The molar ratio of hydroxyalkyl perhydro-s-triazine to acylating agent is such that said ester derivative is produced. Preferable molar ratios of hydroxyalkyl perhydro-s-triazine to acylating agent include ratios from about 10:1 to about 1:10 and most preferably from about 1:1 to about 1:3.

Preferred carboxylic acid derivatives for preparation of said esters of the present invention are fatty acids, either saturated or unsaturated having $C_{4-30}$ carbons. Unsaturated fatty acids include aromatic fatty acids. Examples of ethylenically unsaturated $C_{4-30}$ fatty acids include lauric, nonoic, sebacic, palmitic, stearic, oleic, linoleic and linolenic acid or mixtures thereof.

Ether functionality may be added at those hydroxyalkyl positions that are chosen to be unesterified by use of etherating agents such as employed in a standard Williamson synthesis. The techniques of Au, U.S. Pat. No. 4,266,054 (incorporated herein by reference), either before or after esterification may also be used to incorporate the ether functionality.

The tentacular-perhydro-s-triazines may be formulated with additional compounds such as other surfactants and wetting agents to improve efficiency. Fatty dibasic acid or tribasic acids, fatty alcohols or fatty esters of glycerine, polyethylene gylcols or trialkanolamines may be added to aid film forming and persistency on metal surfaces. Also various dispersants, emulsifiers or anti-emulsifiers may be added as dictated by the end-use. Various scale inhibitors and slimicides or bactericides may also be added in order to maintain a clean metal surface on which the triazine inhibitor can form a protective film.

To aid in the handling and application of the tentacular-perhydro-s-triazine, the tentacular-perhydro-s-triazine plus other optional additives, may be blended with a suitable solvent. For example, polar solvents such as isopropanol or isobutanol, either alone or with water, may be employed when water is the main or continuous portion of the fluid to which the inhibitor is to be added. In situations where flammable solvents cannot be employed, a water emulsion may be prepared using a soap such as, for example, triethanolamine plus oleic acid as an emulsifying agent. When oil is the main or continuous phase of the fluid to which the compound is to be added, the tentacular-perhydro-s-triazine plus optional additives may be dissolved in an oleaginous liquid such as kerosene or in a mixture of one or more organic liquids, for example, hydrocarbons plus one or more polar organic solvents.

The preferred use of the tentacular-perhydro-s-triazines is as a corrosion inhibitor. When employed in a picking bath or other corrosive environment as a corrosion inhibitor, the present invented compounds are merely added to the corrosive fluid in use.

While any amount effective to prevent corrosion may be employed, preferred are amounts from about 0.001 percent to 10 percent by weight based on the weight of crude oil, pickling bath or other fluid (e.g., hydraulic fluid) being protected. Preferred are amounts from about 0.1 percent to about 1 percent.

Iron and steel in contact with an oleaginous liquid containing corrosive agents may be inhibited from corrosion by mixing about one part of the tentacular-perhydro-s-triazines in one million parts of the fluid. More than one part may be employed, with 10,000 parts per million a preferred upper limit. Iron and steel in contact with an oleaginous liquid containing corrosive agent may also be inhibited from corrosion by mixing about 100 ppm of the tentacular-perhydro-s-triazines with an organic carrier liquid such as the mixtures of alcohols and water, alkanolamines and fatty acids or oleaginous liquid such as kerosene to make a fluid composition. Said metal is contacted with the resultant composition to provide a protecting film thereon.

The metal parts of equipment in a wellbore used in the production of a fluid mineral, oil and/or gas from a subterranean formation may be inhibited from corrosion by injecting the tentacular-perhydro-s-triazines down the wellbore. Similarly, the tentacular-perhydro-s-triazines may be dissolved in the organic carrier liquids and thereafter injected down the borehole at sufficient pressure to force the resultant composition back into the formation. Preferably, a portion of the composition is retained therein from whence it leaches out into the fluid during its production.

Treatment to provide protection against corrosion of well equipment is usually carried out by dispersing the tentacular-perhydro-s-triazine corrosion inhibitor in a suitable organic diluent. A typical corrosion inhibitor concentrate consists of 5 percent to 40 percent but usually 30 percent active inhibitor of the tentacular-perhydro-s-triazines, with the balance being either isobutanol, kerosene or 10 percent to 20 percent isobutanol and the balance kerosene. Crude oil produced at the well site or refined petroleum products such as diesel fuel may be substituted for kerosene. Occasionally the 30 percent active inhibitor composition is further diluted by a factor of up to 10 with crude oil or other oleaginous liquid prior to addition to a well. This typically aids in lowering of the viscosity.

Batch treatments are usually used for oil wells. The tentacular-perhydro-s-triazine inhibitor composition typically containing 5 percent to 40 percent of the active inhibitor may be put into the annulus of a cased wellbore provided with tubing. The well is then put back into production, and the active inhibitor present in the annulus gradually mixes with the oil being produced through the tubing.

Squeeze treatments can be effective in oil wells and especially effective in high pressure gas wells. The typical inhibitor composition containing about 30 percent of the tentacular-perhydro-s-triazine active inhibitor is further diluted to an active content of preferably 0.1 percent to 10 percent, more preferably 3 percent to 10 percent with an oleaginous liquid such as crude oil, kerosene or diesel oil. The diluted solution is injected down a wellbore penetrating a subterranean formation and forced back into the formation. The pressure is then released and the well put back into production. The tentacular-perhydro-s-triazine corrosion inhibitor slowly leaches out into the crude oil during production.

Continuous treatment may also be used with oil and gas wells and transmission pipelines. The tentacular-perhydro-s-triazine inhibitor composition is continually metered into the tubing or pipeline with a pump. The concentration of active inhibitor in the produced fluids is preferably between 1 ppm and 1,000 ppm, more preferably between 10 ppm and 100 ppm.

To use the tentacular-perhydro-s-triazines as emulsifying agent, standard methods are employed. Preferably, the emulsive tentacular-perhydro-s-triazines are used in continuous streams.

To use the tentacular-perhydro-s-triazines as a hydraulic fluid (i.e., means for transferring hydraulic pressure), standard methods are employed. The tentacular-perhydro-s-triazines can be employed in combination with other liquids. Preferably, the hydraulic fluid contacts metaliferous surfaces, and thus the hydraulic fluid is preferably a corrosion inhibitor also.

To use the tentacular-perhydro-s-triazines as lubricating agent, standard methods are employed. The lubricative tentacular-perhydro-s-triazine can be employed with other lubricants or compounds. Preferably, the lubricating agent contacts metaliferous surfaces also, and thus the lubricating agent is preferably a corrosion inhibitor as well.

SPECIFIC EMBODIMENTS

The following examples further illustrate the invention.

EXAMPLE 1

1,3,5-Triazine-1,3,5(2H,4H,6H)triethanol Monooleate 1,3,5-tris(2-Hydroxyethyl)perhydro-s-triazine (21.6 g, 0.1 mole) and potassium carbonate (35 g) are combined in a mixture of 50 ml of water and 150 ml of methylene chloride at 0° C. Oleic acid chloride (30 g, 0.1 mole) in 50 ml of methylene chloride is added at a rate such that the reaction mixture is retained at a temperature below about 10° C. After complete addition, the mixture is stirred at 0° C. for 15 hours and then at about 25° C. for an additional 16 hours. The organic layer is separated, dried over magnesium sulfate and concentrated to a yellow oil. Analysis by infrared spectroscopy and nuclear magnetic resonance spectroscopy identify the product as 1,3,5-triazine-1,3,5-(2H,4H,6H)triethanol monooleate.

EXAMPLE 2

Di- and Triesters

The reaction conditions of Example 1 are substantially repeated excepting that the amount of oleic acid chloride reacted is increased to about 2:1 molar ratio and 3:1 molar ratio compared to 1,3,5-tri(2-hydroxyethyl)perhydro-s-triazine, respectively. The compounds prepared are recovered and identified as 1,3,5-triazine-1,3,5-(2H,4H,6H)triethanol dioleate and 1,3,5-triazine-1,3,5-(2H,4H,6H)triethanol trioleate.

EXAMPLE 3

1,3,5-Triazine-1,3,5(2H,4H,6H)triethanol Monooleate by Improved Method

A mixture of 20 g of 1,3,5-tris-hydroxyethyl perhydro-s-triazine from the method of Paquin, Ber., 82, 316 (1949) and 0.30 g (5.8 mole percent) of powdered KOH is heated at 80° C. under reduced pressure (less than 0.1 mm) for 6 hours. Methyl oleate (30g ) from acid-catalyzed esterification of oleic acid in methanol is then added and the resulting mixture (in two phases) is stirred at 80° C. under the reduced pressure overnight. The homogeneous material which is obtained is dissolved in CH$_2$Cl$_2$, washed with water, dried over potassium carbonate, then is concentrated into a light yellow oil of 41 g (84.9 percent of theory). Both the infrared (1745 cm$^{-1}$) and nuclear magnetic resonance spectra are consistent with the desired 1,3,5-triazine-1,3,5-(2H,4H,6H)triethanol monooleate.

EXAMPLE 4 WITH COMPARATIVE EXAMPLE

Corrosion Testing

A synthetic crude oil is simulated by combining equal volumes of heavy mineral oil and aqueous 2 percent brine solution (containing primarily chloride salts of sodium and calcium). The synthetic crude oil is purged with a nitrogen stream then saturated with carbon dioxide. Hydrogen sulfide is generated in situ at a concentration of 50 ppm by addition of 6.15 ml of glacial acetic acid and sodium sulfide-9-hydrate (1.1 g) to 3 liters of brine.

The inhibitors further identified in Table I are added to the synthetic crude oil to provide an inhibitor concentration of 100 ppm. A sample of the solution (320 ml) is added to a sealable glass bottle containing a mild steel coupon (4.4 g). The bottle is sealed and agitated for 72 hours at 65° C. The weight losses of coupons treated in this manner are compared to those of similar coupons in fluids containing no inhibitor. The percent protection is calculated as percent weight loss/percent weight loss of control ×100. Results are contained in Table I.

TABLE I

| Inhibitor | % Protection |
| --- | --- |
| 1,3,5-triazine-1,3,5-(2H,4H,6H)—triethanol monooleate (Example 1) | 77 |
| 1,3,5-triazine-1,3,5-(2H,4H,6H)—triethanol dioleate | 77 |
| 1,3,5-triazine-1,3,5-(2H,4H,6H)—triethanol trioleate | 72 |
| 1,3,5-tris(2-hydroxyethyl)perhydro-s-triazine (Comparative, not of the invention) | 11 |

It is seen that the esterified compounds of the present invention exhibited improved corrosion protection compared to unesterified compounds.

EXAMPLE 5

A. Preparation of 1,3,5-tris(2-Mercaptoethyl)perhydro-s-triazine

If a solution of 0.5 mole of formaldehyde (37 percent generally aqueous dissolved in 250 ml of methanol) is added dropwise to 0.5 mole of 2-aminoethanethiol (Aldrich) mixed with 250 ml of methanol, at 30° C. with stirring, reaction occurs. The reaction mixture is stirred overnight. The solvent is next removed by distillation under vacuum, and the desired product is recovered.

B. Derivatization to 1,3,5-Triazine-1,3,5-(2H,4H,6H)triethanethiol Monooleate

If the 1,3,5-tris(2-mercaptoethyl)perhydro-s-triazine (0.1 mole) is mixed with oleic acid chloride (30 g, 0.1 mole) by the general procedure of Example 1, reaction occurs. The product is identified as substantially the monooleate.

C. Derivatization to Corresponding Di- and Trioleates

If 0.1 mole of the 1,3,5-tris(2-mercaptoethyl)perhydro-2-triazine is mixed respectively with 60 g or 90 g of oleic acid chloride by the general procedure of Example 2, reaction occurs. The product is, respectively, the corresponding di- or trioleate.

EXAMPLE 6

Preparation of 1,3,5-tris(2-Bis(methyl)aminoethyl)perhydro-s-triazine

If a solution of 0.5 mole of formaldehyde (37 percent generally aqueous dissolved in 250 ml of methanol) is added dropwise to 0.5 mole of N,N-dimethylethylenediamine (asymmetrical)(Aldrich), mixed with 250 ml of methanol, at 30° C. with stirring, reaction occurs. The reaction mixture is stirred overnight. The solvent is next removed by distillation under vacuum and the desired product is recovered.

EXAMPLE 7

Preparation of 1,3,5-tris(2-(4-Morpholino)aminoethylperhydro-s-triazine

If a solution of 0.5 mole of formaldehyde (37 percent generally aqueous dissolved in 250 ml of methanol) is added dropwise to 0.5 mole of 4-(2-aminoethyl)morpholine (Aldrich), mixed with 250 ml of methanol, at 30° C. with stirring, reaction occurs. The reaction mixture is stirred overnight. The solvent is next removed by distillation under vacuum and the desired product is recovered.

We claim:

1. A process for inhibiting corrosion of metals in contact with corrosive fluids comprising contacting the metal with an effective corrosion inhibiting amount of a tentacular-perhydro-s-triazine under conditions sufficient to inhibit corrosion, wherein the tentacular-perhydro-s-triazine corresponds to the formula:

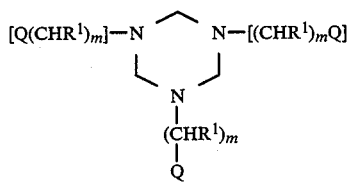

wherein Q is separately at each occurrence a $C_{1-60}$ moiety selected from the group consisting of acyclic secondary and tertiary amino, heterocyclic secondary and tertiary amino, hydroxy-substituted and mercapto-substituted acyclic and heterocyclic secondary and tertiary amino, amido, acyl, thioacyl, ether, thioether, ester, ester-ether, thioester, and mercapto moieties; $R^1$ is separately at each occurrence hydrogen, or a $C_{1-20}$ alkyl; and m is separately at each occurrence an integer from one to about twenty.

2. The process of claim 1 wherein the tentacular-perhydro-s-triazine is an ester or ester-ether derivative of a tris-hydroxyalkyl perhydro-s-triazine.

3. The process of claim 1 wherein the tentacular-perhydro-s-triazine is 1,3,5-(2-bis(methyl)aminoethyl)perhydro-s-triazine.

4. The process of claim 1 wherein the tentacular-perhydro-s-triazine is 1,3,5-tris-(2-(4-morpholino)aminoethyl)perhydro-s-triazine.

5. The process of claim 1 wherein the tentacular-perhydro-s-triazine is employed in an amount from about one part per million parts fluid to about 10,000 parts per million parts fluid to inhibit the corrosion of iron and steel.

6. The process of claim 1 wherein the tentacular-perhydro-s-triazine is dissolved in a solvent before the addition of the inhibitor to the corrosive fluid.

7. The process of claim 1 wherein the tentacular-perhydro-s-triazine is employed in an amount from about 0.001 percent to about 10 percent by weight based on the weight of fluid being protected.

8. The process of claim 7 wherein the tentacular-perhydro-s-triazine is employed in an amount from about 0.1 percent to about 1 percent by weight based on the weight of fluid being protected.

9. A process for inhibiting corrosion of metals in contact with corrosive fluids comprising contacting the metal with an effective corrosion inhibiting amount of a tentacular-perhydro-s-triazine under conditions sufficient to inhibit corrosion, wherein the tentacular-perhydro-s-triazine is an ester or ester-ether derivative of a tris-hydroxyalkyl perhydro-s-triazine corresponding to the formula:

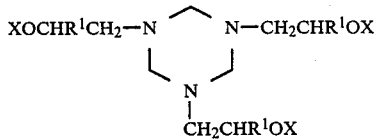

wherein
$R^1$ is hydrogen, methyl, or ethyl; and
X is hydrogen, $-(CH_2CHR^1O)_nR^5-$ or $-C(O)R^5$, where n is a number from zero to about 4, and $R^5$ is alkyl, cycloalkyl, alkenyl or aryl of up to about 30 carbons.

10. The process of claim 9 wherein $R^5$ is a remnant of lauric, nonoic, sebacic, palmitic, stearic, oleic, linoleic, or linolenic acid or a mixture thereof.

11. The process of claim 10 wherein $R^5$ is a remnant of oleic acid.

12. The process of claim 11 wherein the ester derivative of a tris-hydroxyalkyl perhydro-s-triazine is selected from the group consisting of 1,3,5-triazine-1,3,5-(2H,4H,6H)triethanol monooleate, 1,3,5-triazine-1,3,5-(2H,4H,6H)triethanol dioleate, and 1,3,5-triazine-1,3,5-(2H,4H,6H)triethanol trioleate.

* * * * *